US009750422B2

(12) United States Patent
Zino et al.

(10) Patent No.: US 9,750,422 B2
(45) Date of Patent: Sep. 5, 2017

(54) CATHETER WITH TRANSVERSE BRANCHES

(71) Applicant: BIOSENSE WEBSTER (ISRAEL) LTD., Yokneam (IL)

(72) Inventors: Eliahu Zino, Atlit (IL); Noam Igra, Hertzillya (IL); Shmuel Auerbach, Kerem Maharal (IL); Roy Urman, Karkur (IL); Yaniv Ben Zriham, Binyamina (IL); Assaf Pressman, Pardes Hanna-Karkur (IL)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 209 days.

(21) Appl. No.: 14/603,415

(22) Filed: Jan. 23, 2015

(65) Prior Publication Data
US 2015/0223715 A1 Aug. 13, 2015

Related U.S. Application Data

(60) Provisional application No. 61/938,883, filed on Feb. 12, 2014.

(51) Int. Cl.
*A61B 5/042* (2006.01)
*A61B 18/14* (2006.01)
(Continued)

(52) U.S. Cl.
CPC .......... *A61B 5/0422* (2013.01); *A61B 5/6859* (2013.01); *A61B 18/1492* (2013.01); *A61B 2017/00044* (2013.01); *A61B 2017/00053* (2013.01); *A61B 2018/0016* (2013.01); *A61B 2018/00214* (2013.01); *A61B 2018/00351* (2013.01); *A61B 2018/00577* (2013.01);
(Continued)

(58) Field of Classification Search
CPC ... A61B 5/6852; A61B 5/6859; A61B 5/6869; A61B 18/1492; A61B 5/0422; A61N 1/056
USPC ...................... 600/374, 381; 606/41; 607/122
See application file for complete search history.

(56) References Cited

U.S. PATENT DOCUMENTS 3,866,615 A * 2/1975 Hewson ............... A61N 1/0587
607/10
4,386,615 A * 6/1983 Sowton ................. A61N 1/056
607/125
(Continued)

FOREIGN PATENT DOCUMENTS

EP 0727183 A1 8/1996
EP 2641556 A1 9/2013

OTHER PUBLICATIONS

U.S. Appl. No. 61/938,883, filed Feb. 12, 2014.
European Search Report dated Jun. 15, 2015 for corresponding Application No. EP15154737.

*Primary Examiner* — Lee S Cohen
(74) *Attorney, Agent, or Firm* — Louis J. Capezzuto (57) ABSTRACT

Apparatus, including a flexible insertion tube, having a distal segment that is configured to be inserted into a body organ. A plurality of elastic branches are connected to the distal segment of the insertion tube at different, respective locations and extend transversely away from the insertion tube at the respective locations. There are one or more respective electrodes disposed on each of the elastic branches and there are conductors traversing the elastic branches so as to couple the electrodes to the insertion tube.

66 Claims, 7 Drawing Sheets

(51) Int. Cl.
 *A61B 5/00* (2006.01)
 *A61B 18/00* (2006.01)
 *A61B 17/00* (2006.01)
 *A61B 34/20* (2016.01)

(52) U.S. Cl.
 CPC ............ *A61B 2018/00839* (2013.01); *A61B 2034/2051* (2016.02); *A61B 2562/125* (2013.01); *Y10T 29/49169* (2015.01)

(56) References Cited

U.S. PATENT DOCUMENTS

| | | | | |
|---|---|---|---|---|
| 4,660,571 A * | 4/1987 | Hess | ............... | A61B 5/0422 604/105 |
| 5,282,845 A * | 2/1994 | Bush | ............... | A61N 1/0587 607/127 |
| 5,855,592 A * | 1/1999 | McGee | ............... | A61N 1/3918 600/374 |
| 6,006,139 A * | 12/1999 | Kruse | ............... | A61N 1/056 600/375 |
| 6,029,091 A * | 2/2000 | de la Rama | ....... | A61B 18/1492 600/374 |
| 6,148,238 A * | 11/2000 | Rutten | ............... | A61N 1/057 607/126 |
| 6,163,716 A * | 12/2000 | Edwards | ............... | A61B 5/0422 128/898 |
| 6,574,492 B1 * | 6/2003 | Ben-Haim | ........... | A61B 5/0215 600/374 |
| 6,684,109 B1 * | 1/2004 | Osypka | ................ | A61N 1/0563 607/122 |
| 7,191,018 B2 * | 3/2007 | Gielen | ............. | A61M 5/14276 607/116 |
| 7,561,907 B2 * | 7/2009 | Fuimaono | ............ | A61B 5/0422 600/374 |
| 8,538,516 B2 * | 9/2013 | Lee | ................... | A61B 5/04001 607/2 |
| 8,744,599 B2 * | 6/2014 | Tegg | ................... | A61B 5/0422 600/374 |
| 8,926,528 B2 * | 1/2015 | Govari | ............... | A61B 19/5244 600/585 |

* cited by examiner

CATHETER WITH TRANSVERSE BRANCHES

CROSS-REFERENCE TO RELATED APPLICATION

This application claims the benefit of U.S. Provisional Patent Application 61/938,883, filed Feb. 12, 2014, which is incorporated herein by reference.

FIELD OF THE INVENTION

The present invention relates generally to a catheter having a number of electrodes, and specifically to the design and operation of such a catheter.

BACKGROUND OF THE INVENTION

Catheters with electrodes are used in a number of medical procedures, such as investigating or operating on a region of the heart. In these procedures the electrodes may be used, for example, to inject known currents (typically for catheter tracking purposes), to measure electropotentials of specific regions of the heart, and/or to ablate the regions. While catheters with a small number of electrodes, or even with a single electrode, may be used for such procedures, certain software algorithms may increase the value of having large number of electrodes on the catheter. Such an arrangement allows a physician using the catheter to select which of one or more of the electrodes may be used, and also to select if the electrodes are to be used simultaneously or not.

SUMMARY OF THE INVENTION

An embodiment of the present invention provides apparatus, including:

a flexible insertion tube, having a distal segment that is configured to be inserted into a body organ;

a plurality of elastic branches connected to the distal segment of the insertion tube at different, respective locations and extending transversely away from the insertion tube at the respective locations;

one or more respective electrodes disposed on each of the elastic branches; and conductors traversing the elastic branches so as to couple the electrodes to the insertion tube.

Typically, each of the elastic branches consists of an elastic region and an inelastic region. The elastic region may be closer to the flexible insertion tube than the inelastic region. On application of a bending force to a branch, the inelastic region typically aligns to be parallel to the insertion tube. On removal of the bending force the inelastic region typically returns to extending transversely away from the insertion tube.

In a disclosed embodiment the different respective locations of a pair of the elastic branches lie on a cross-sectional circle of the flexible insertion tube.

In a further disclosed embodiment, for a cross-sectional circle of the flexible insertion tube only one of the elastic branches is connected to the circle.

In a yet further disclosed embodiment the elastic branches and the distal segment lie in a common flat plane. Alternatively, the elastic branches and the distal segment lie in a plurality of planes.

The elastic branches may be orthogonal to the distal segment. Alternatively, the elastic branches may extend non-orthogonally from the distal segment.

In an alternative embodiment the body organ consists of a heart, and the one or more respective electrodes are configured to acquire an electrocardiograph (ECG) signal from the heart. Alternatively or additionally the one or more respective electrodes are configured to ablate tissue of the heart.

The distal segment in a relaxed state may form a straight line or may form a curve.

There is further provided, according to an embodiment of the present invention, a method, including:

providing a flexible insertion tube, having a distal segment that is configured to be inserted into a body organ;

connecting a plurality of elastic branches to the distal segment of the insertion tube at different, respective locations so that the branches extend transversely away from the insertion tube at the respective locations;

disposing one or more respective electrodes on each of the elastic branches; and arranging conductors to traverse the elastic branches so as to couple the electrodes to the insertion tube.

The present disclosure will be more fully understood from the following detailed description of the embodiments thereof, taken together with the drawings, in which:

DETAILED DESCRIPTION OF EMBODIMENTS

Overview

Catheters for performing a medical procedure typically have as small a diameter as possible so as to reduce trauma to a patient undergoing the procedure. However, the small diameter of the catheter limits the number of structures that may be attached to the shaft of the catheter. Furthermore, the catheter may be advanced through the body of the patient using an elongated sheath, and the sheath may restrict the structures which can be retracted back into the sheath. Thus, in the case of a catheter using a large number of electrodes, such as a catheter used for acquiring numbers of simultaneous electrocardiograph (ECG) signals, prior art catheters may be relatively large in order to accommodate the large number of electrodes.

Embodiments of the present invention solve these problems by providing a catheter with a relatively small diameter flexible insertion tube, which may be considered to act as the spine of the catheter. Connected to a distal segment of the tube are a plurality of elastic branches which extend transversely away from the tube. One or more electrodes are disposed on the branches, and conductors traverse the branches and the insertion tube, so as to couple the electrodes to a proximal end of the tube.

By configuring the catheter branches to be elastic, they are able to bend in towards the catheter spine. Thus, in operation, the catheter may be inserted into, and removed from, an organ such as the heart via a relatively small diameter sheath, which is prepositioned in the organ. While in the sheath, the branches bend in towards the spine. Once inside the organ, the branches can unbend and the electrodes of the branches may be used to transfer electrical signals to/from the organ.

Detailed Description

Figure 1A:
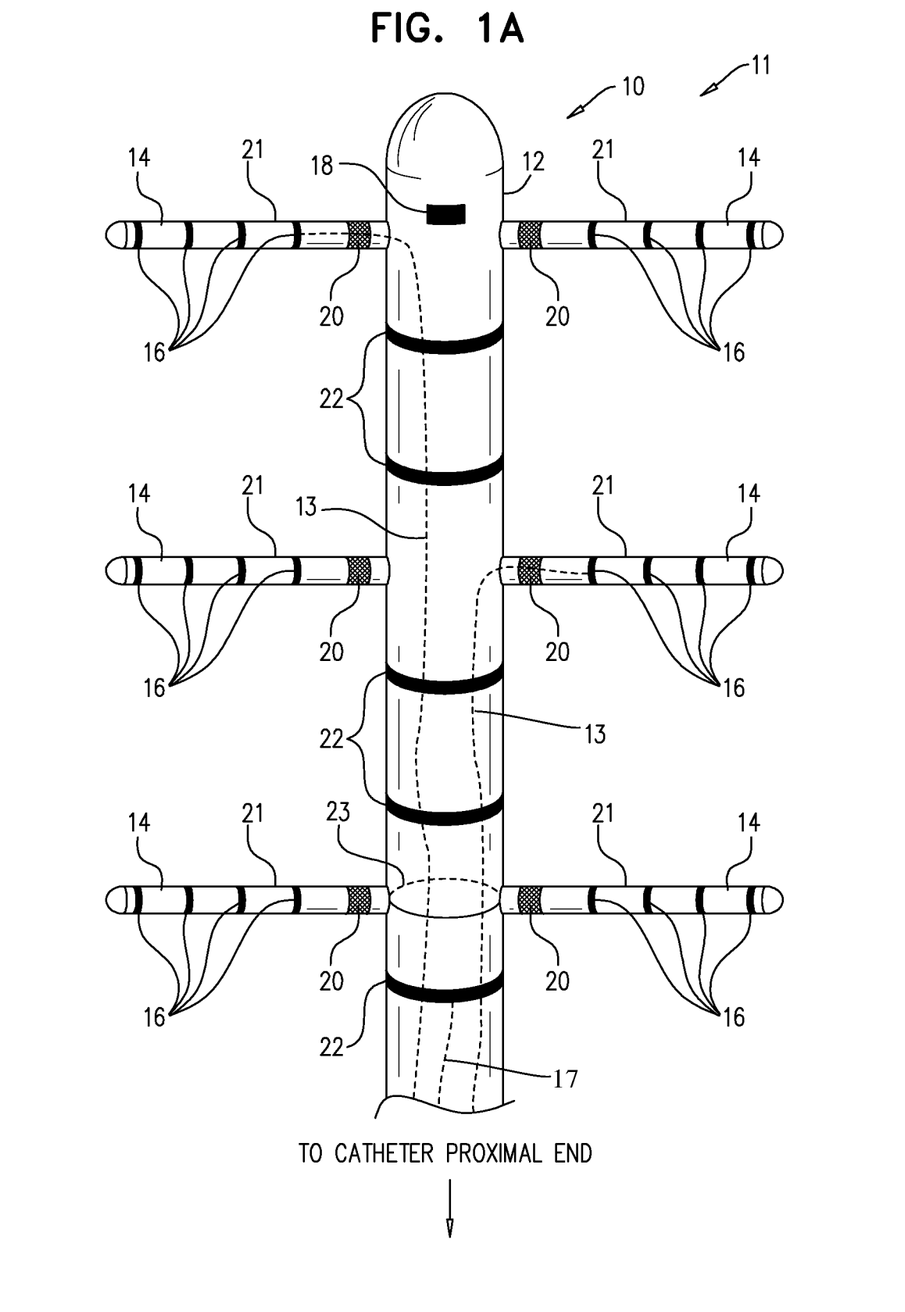
FIGS. 1A and 1B illustrate schematically a catheter distal portion in two states, according to an embodiment of the present invention.
Figure 1B:
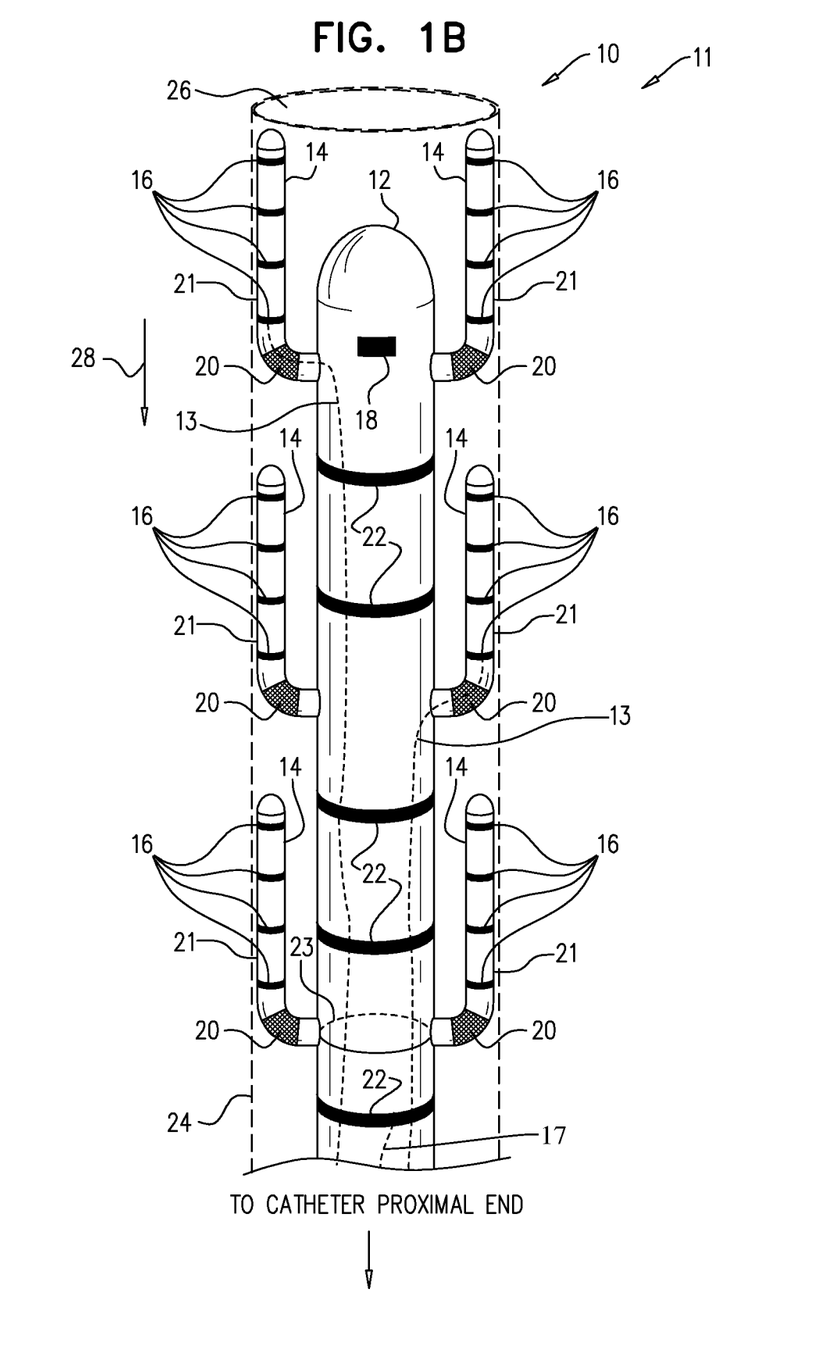

FIGS. 1A and 1B illustrate schematically a distal portion 10 of a flexible insertion tube 11 in two states, according to an embodiment of the present invention. FIG. 1A illustrates the distal portion in an unfolded, relaxed, or unbent, state; FIG. 1B illustrates the distal portion in a folded, or bent, state. Tube 11 may be used as a catheter, and is also referred to herein as catheter 11. Distal portion 10 comprises a distal segment 12, which is typically generally cylindrical and which acts as a main spine of the flexible insertion tube, so that it is also referred to herein as main spine 12. In the relaxed state of tube 11, the spine forms a straight line. A plurality of generally similar elastic branch elements 14, also typically generally cylindrical, and also referred to herein as elastic branches 14, are connected to the distal segment. The connection of the branch elements to the main spine is configured so that at any given junction the two entities, the element and the spine, are transverse to each other, so that the branch elements protrude from the distal segment.

As is illustrated in the figures, in distal portion 10 elements 14 are paired together, so that the locations of the junctions between any given pair of elements 14 with spine 12 lie on a cross-sectional circle 23 of the spine. (For clarity and simplicity, only one such cross-sectional circle is shown in the figures.) In some embodiments the branch elements are orthogonal to spine 12, so that, for example, if the junctions are on a diameter of the cross-sectional circle, elements 14 subtend an angle of 180° to each other. Alternatively, junctions of the orthogonal branch elements may lie on the cross-sectional circle, but the elements may subtend an angle other than 180° to each other, for example angles in the range of 45°-179°. In other embodiments at least some of the branch elements are not orthogonal to the spine, but rather subtend an angle to the spine that is greater than, or less than, 90°.

Each branch element 14 comprises one or more, typically a multiplicity, of electrodes 16 that may be formed as a ring around the element. Alternatively or additionally, at least some of electrodes 16 may be formed as flat structures on the branch element. The material of spine 12, elements 14, and electrodes 16 are selected to be biocompatible. The electrodes are connected, at a proximal end of catheter 11, via respective conductors 13 in the elements and in the spine, to an operating console which is able to receive electrical signals from, and/or transmit electrical signals to, the electrodes. For simplicity only two conductors 13 are shown in FIGS. 1A and 1B. A suitable operating console is provided in the Carto® system, produced by Biosense Webster, of Diamond Bar, Calif. The console is typically configured to provide other functions for the distal portion, such as tracking the distal portion. The console is not shown in FIGS. 1A and 1B, but is shown, and console functions are described, with reference to FIG. 3 below.

Typical dimensions of spine 12 are approximately 1 m in length and 1.5 mm-2 mm in diameter (only the distal portion of the spine is shown in the figures), and in some embodiments ring electrodes 22 are also formed around spine 12. Ring electrodes 22 are connected via respective conductors 17 (only one of which is shown in the figures) to the operating console. Typical dimensions of elements 14 are approximately 1.5 cm-2 cm in length and 1 mm diameter. However, the lengths and diameters of spine 12 and elements 14 may be larger or smaller than these values.

Distal portion 10 is configured to be inserted into an organ, such as the heart, of a patient, so that all parts of the distal portion are formed from biocompatible materials. In order to track the location and orientation of the distal portion during the insertion, the distal portion typically comprises one or more position-sensors 18. In some embodiments sensors 18 are operative by generating signals in response to external magnetic fields interacting with the sensor. Sensors of this type are provided in the Carto® system, referenced above.

As stated above, at the junction between elements 14 and spine 12 the elements and the spine are transverse to each other. In addition, close to the junction each element 14 comprises a region 20 which allows the element to elastically bend from its cylindrical state. Region 20 is configured to be more flexible and elastic than the remainder of element 14, which is relatively inelastic and comprises an inelastic region 21. Consequently, under a force such as that exemplified below with respect to the description of FIG. 1B, element 14 elastically bends at region 20 rather than at another section of the element. On release of the bending force, the elastic properties of region 20 cause the element to return to its cylindrical shape.

In order to insert distal portion 10 into the organ of the patient referred to above, typically a sheath 24 (FIG. 1B) is first inserted into the organ. Sheath 24 typically has an internal diameter up to approximately 4 mm, depending on the size of spine 12 and elements 14, so that the diameter of the sheath may be smaller than 4 mm. Distal portion 10 is then inserted into the sheath, and the diameter of the sheath constrains elements 14, by exerting a force on the elements, to bend. The flexible and elastic character of region 20 constrains the elements to bend at the region, so that distal portion 10, with elements 14 in their bent state, may traverse sheath 24. If sheath 24 has been inserted into the patient so that a sheath distal end 26 terminates at the patient's organ, then distal portion 10 traverses the sheath until it exits the sheath, and enters the organ. On exiting the sheath elements 14 recover their cylindrical form, by unbending at elastic region 20.

FIG. 1B illustrates the case of catheter distal portion 10 being withdrawn, in a direction of arrow 28, from the patient's organ. In this case the catheter distal portion 10 has been withdrawn via sheath distal end 26 into sheath 24. The withdrawal exerts a force on elements 14, causing the elements to elastically bend at region 20. In contrast to the situation where the catheter distal portion is inserted into the patient's organ, FIG. 1B illustrates the case where the catheter distal portion is being withdrawn from the organ, so that bent elements 14 typically "face towards" sheath distal end 26. As is illustrated in the figure, within the sheath inelastic region 21 is parallel to spine 12. In the case of catheter distal portion 10 entering into the patient's organ, elements 14 typically "face away from" sheath distal end 26.

Figure 2A:
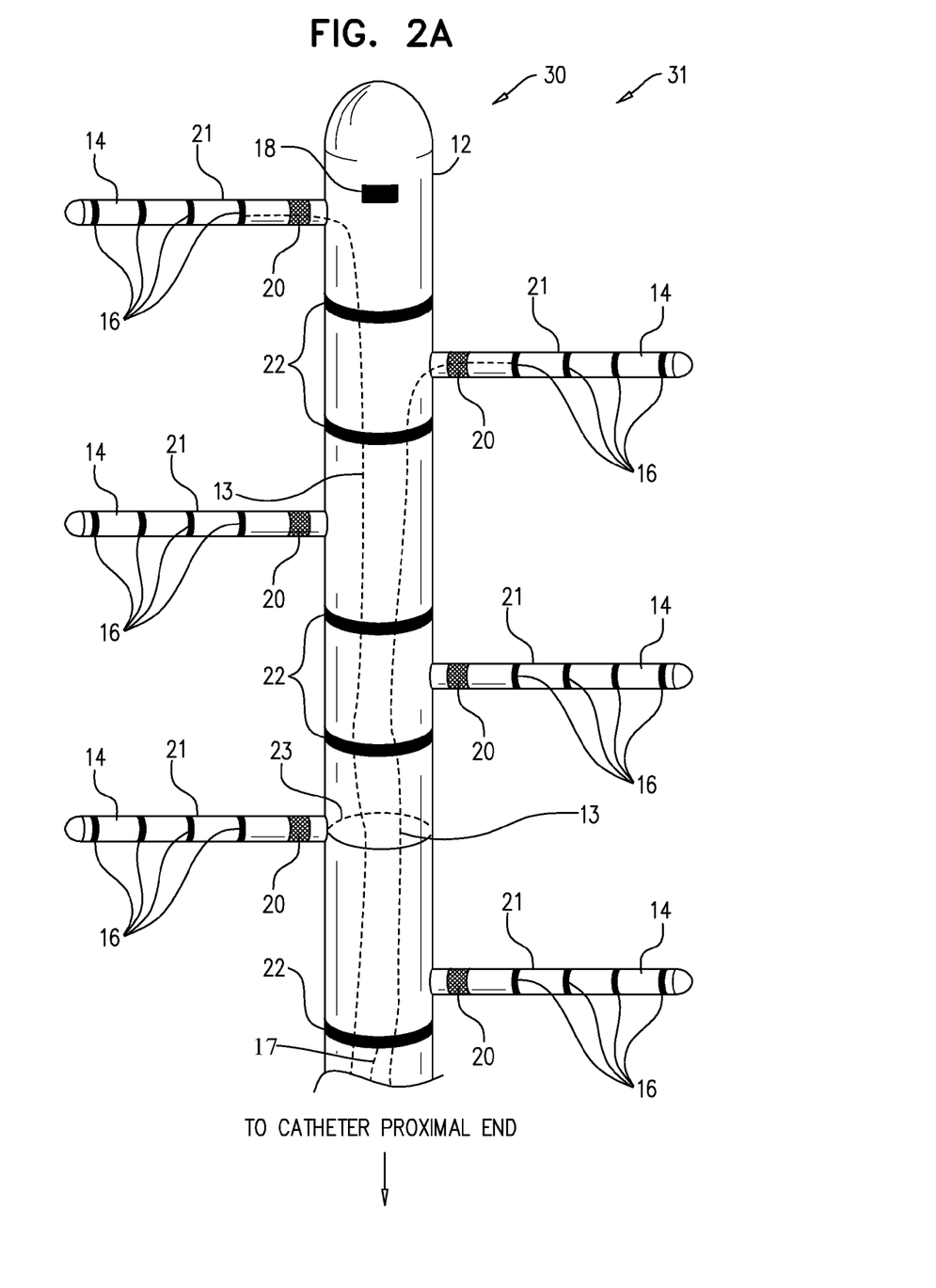
FIGS. 2A and 2B illustrate schematically a catheter distal portion in two states, according to an alternative embodiment of the present invention.
Figure 2B:
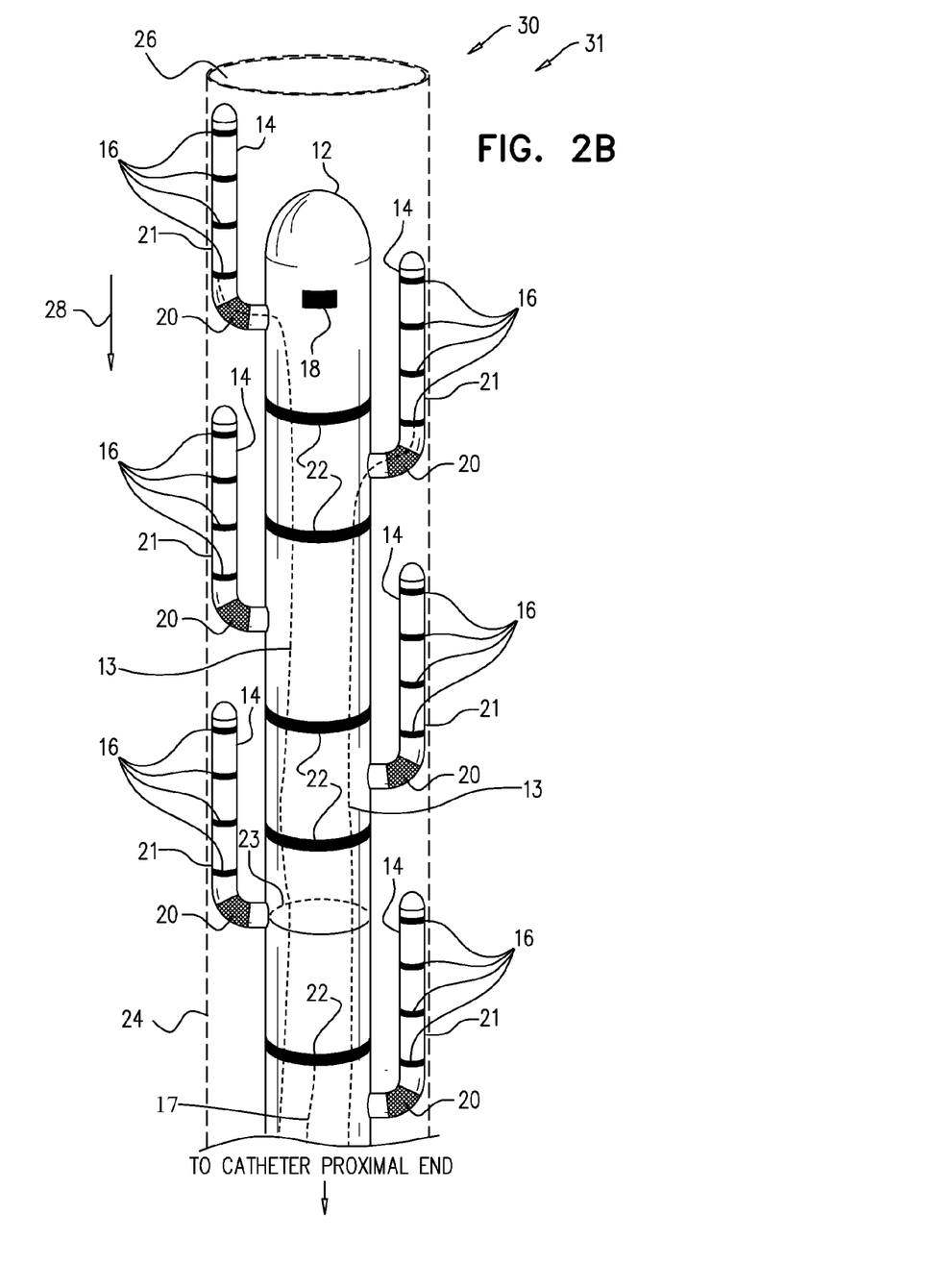

FIGS. 2A and 2B illustrate schematically a distal portion 30 of a flexible insertion tube 31 in two states, according to an alternative embodiment of the present invention. FIG. 2A illustrates distal portion 30 in an unbent state; FIG. 2B illustrates the distal portion in a bent state. Tube 31 may be used as a catheter, and is also referred to herein as catheter 31. Apart from the differences described below, the operation of distal portion 30 is generally similar to that of distal portion (FIGS. 1A and 1B), and elements indicated by the same reference numerals in both distal portions 10 and 30 are generally similar in construction and in operation. In contrast to distal portion 10, where elements 14 are arranged in pairs, each pair joining spine 12 at a common diameter of the spine, elements 14 in distal portion 30 are arranged in a staggered configuration along spine 12. In other words, each element 14 joins spine 12 at a unique diameter of the spine. The staggered arrangement of elements 14 in distal portion 30 may reduce the possibility of a blood clot forming at the junction, compared to the local junctions of distal portion 10.

In some embodiments elements 14 have approximately the same dimensions and numbers of electrodes, and in the unbent state of distal portions 10 and 30 the elements are in a common flat plane defined by spine 12, when the spine is a straight line. However, other embodiments of the present invention may have elements 14 differing from each other in dimensions, and/or may have differing numbers of electrodes 16 in each element 14, and/or may lie in more than one plane defined by spine 12.

Figure 3:
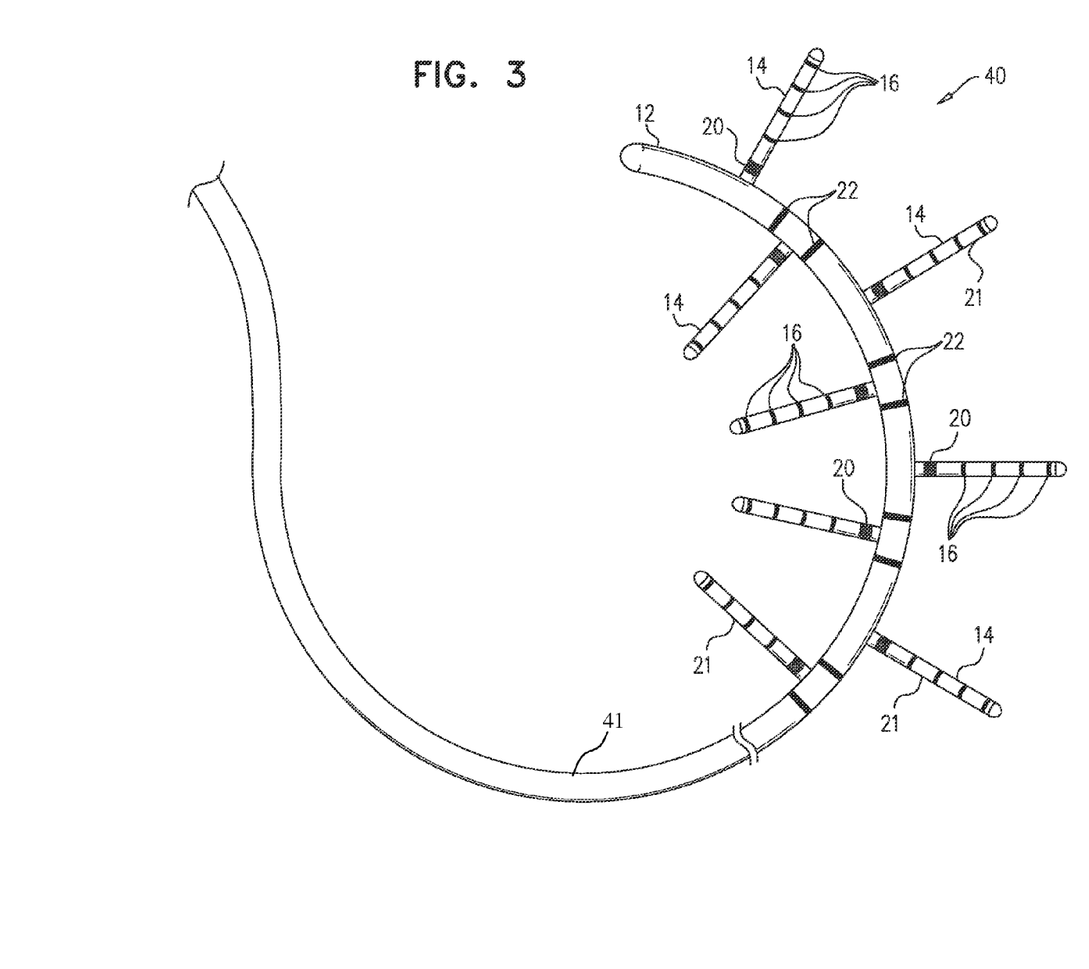
FIG. 3 illustrates schematically a distal portion of a flexible insertion tube, according to an embodiment of the present invention.

FIG. 3 illustrates schematically a distal portion 40 of a flexible insertion tube 41 once it has exited sheath distal end 26, according to an embodiment of the present invention. For simplicity sheath 26 is not shown in FIG. 3. Tube 41 may be used as a catheter, and is also referred to herein as catheter 41. Apart from the differences described below, the operation of distal portion 40 is generally similar to that of distal portion (FIGS. 1A and 1B), and elements indicated by the same reference numerals in both distal portions 10 and 40 are generally similar in construction and in operation.

In contrast to distal portion 10, spine 12 of distal portion 40 in its relaxed state, i.e., when it is outside sheath 26, is in the form of a section of a circle, or other plane curved structure, so that catheter 41 may be in the form of a lasso catheter, available in the Carto® system, referenced above. By way of example, spine 12 and branches 14 are assumed to lie in a common plane, the plane of the paper.

Figure 4:
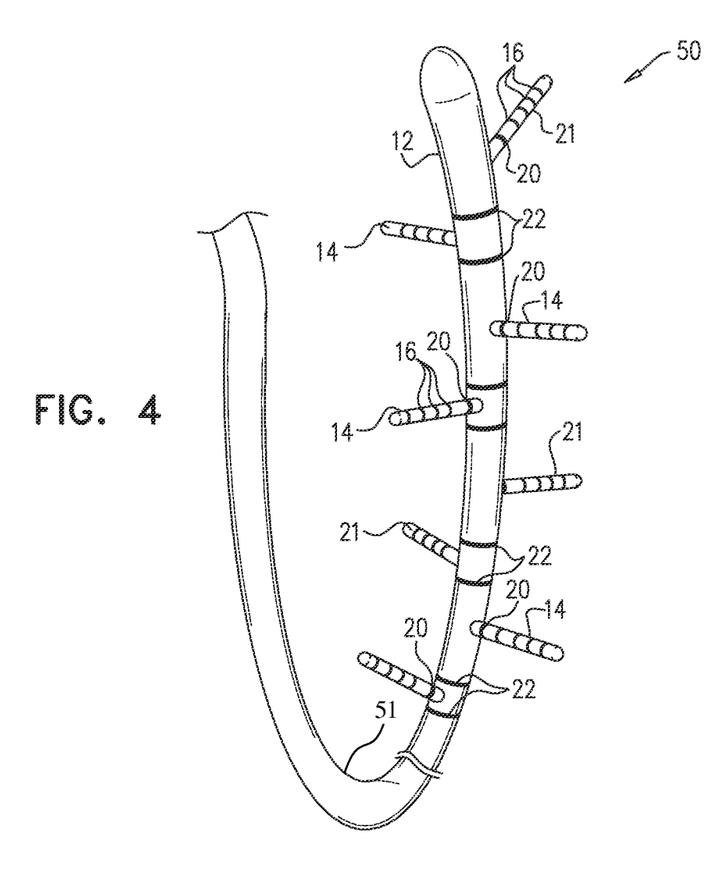
FIG. 4 illustrates schematically a distal portion of a flexible insertion tube, according to an alternative embodiment of the present invention.

FIG. 4 illustrates schematically a distal portion 50 of a flexible insertion tube 51 once it has exited sheath distal end 26, according to an alternative embodiment of the present invention. For simplicity sheath 26 is not shown in FIG. 4. Tube 51 may be used as a catheter, and is also referred to herein as catheter 51. Apart from the differences described below, the operation of distal portion 50 is generally similar to that of distal portion 40 (FIG. 3), and elements indicated by the same reference numerals in both distal portions 40 and 50 are generally similar in construction and in operation.

As for distal portion 40, spine 12 of distal portion forms a plane curved figure in its relaxed state. However, in contrast to distal portion 40, branches 14 and spine 12 of distal portion 50 do not lie in a common plane, but rather lie in different planes. In one embodiment, at least some of branches 14 are orthogonal to the plane of spine 12 in its relaxed state.

There are a number of possible structures for spine 12. For example, the shape of spine 12, and typically distal portion 10 or 30, may be configured to be variable by incorporating one or more wires into the spine, the wires terminating in a shape control at the proximal end of the catheter. Such a variably shaped catheter is available in the Carto® system, referenced above. Other possible structures for spine 12 will be apparent to those having ordinary skill in the art, and all such structures are assumed to be included in the scope of the present invention.

Figure 5:
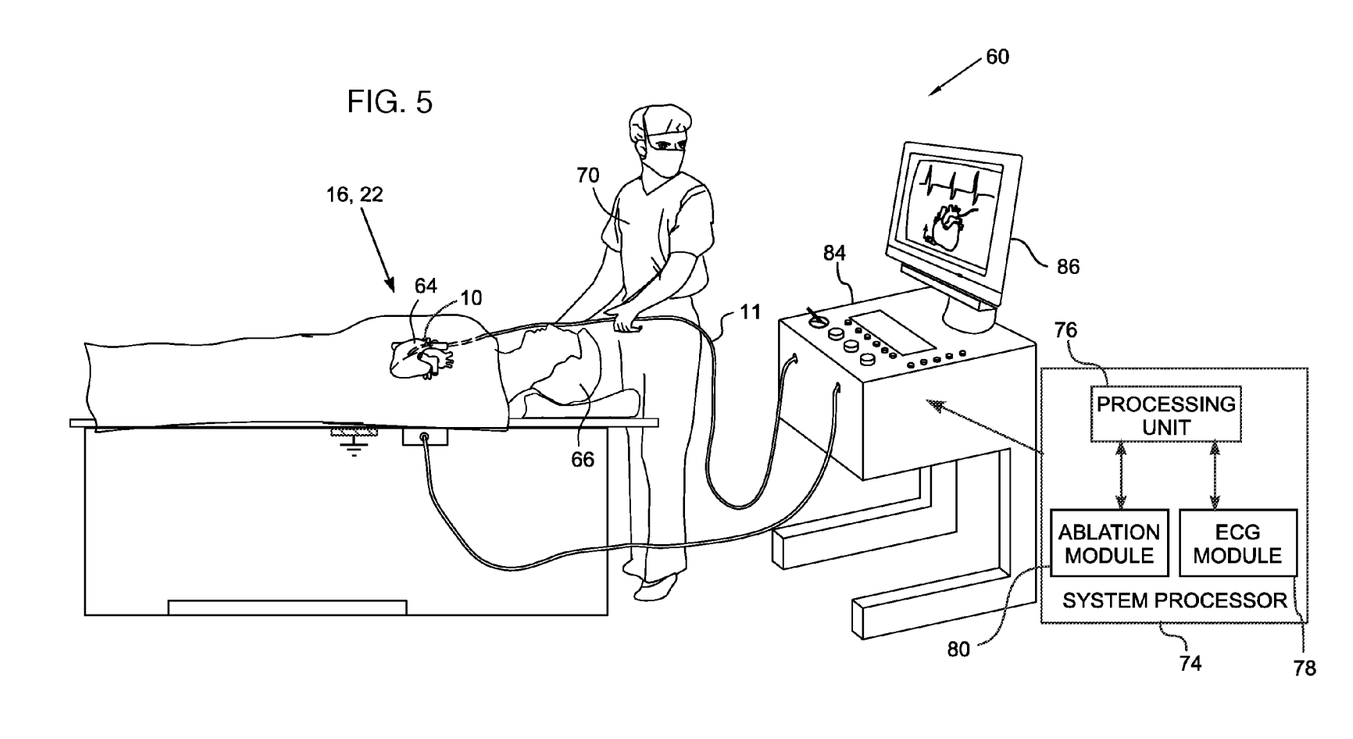
FIG. 5 is a schematic illustration of a medical procedure system, according to an embodiment of the present invention.

Reference is now made to FIG. 5, which is a schematic illustration of a medical procedure system 60 using catheter 11 or catheter 31, according to an embodiment of the present invention. For clarity, FIG. 3 has been drawn assuming that catheter 11 is used in a diagnostic medical procedure on a heart 64 of a patient 66. Those having ordinary skill in the art will be able to adapt the following description, mutatis mutandis, for the case of catheter 31 being used in a, medical procedure that is not diagnostic.

The following description assumes that electrodes 16 and/or 22 of catheter 11 sense intra-cardiac ECG (electro-cardiograph) signals from heart 64. Alternatively or additionally, at least some of the electrodes may be configured to ablate tissue of the heart. The signal sensing and/or ablation is performed after insertion of distal portion 10 into the heart by a medical professional 70.

System 60 may be controlled by a system processor 74, comprising a processing unit 76 communicating with an ECG module 78 and an ablation module 80. The modules enable the processing unit to provide the ECG and ablation functionality described above, as well as other functionality such as analysis and collation of results. Processor 74 may be mounted in a console 84, which comprises operating controls which typically include a pointing device such as a mouse or trackball. Professional 74 uses the pointing device to interact with the processor, which, inter alia, may be used to present results produced by system 60 to the professional on a screen 86.

Processor 74 uses software stored in a memory of the processor to operate system 60. The software may be downloaded to processor 74 in electronic form, over a network, for example, or it may, alternatively or additionally, be provided and/or stored on non-transitory tangible media, such as magnetic, optical, or electronic memory.

Processor 74 typically comprises other modules, such as a probe tracking module that may be coupled to position sensors 18, and a force module that measures a force on distal portion 10. For simplicity, such modules are not shown in FIG. 1. The Carto® system referenced above uses such modules.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
a flexible insertion tube, having a distal segment that is configured to be inserted into a body organ;
a plurality of elastic branches connected to the distal segment of the insertion tube at different, respective locations and extending transversely away from the insertion tube at the respective locations;
one or more respective electrodes disposed on each of the elastic branches; and
conductors traversing the elastic branches so as to couple the electrodes to the insertion tube;
wherein each of the elastic branches comprises an elastic region and an inelastic region.

2. The apparatus according to claim 1, wherein the elastic region is closer to the flexible insertion tube than the inelastic region.

3. The apparatus according to claim 1, wherein on application of a bending force to the each branch, the inelastic region aligns to be parallel to the insertion tube.

4. The apparatus according to claim 3, wherein on removal of the bending force the inelastic region returns to extending transversely away from the insertion tube.

5. The apparatus according to claim 1, wherein the different respective locations of a pair of the elastic branches lie on a cross-sectional circle of the flexible insertion tube.

6. The apparatus according to claim 1, wherein for a cross-sectional circle of the flexible insertion tube only one of the elastic branches is connected to the circle.

7. The apparatus according to claim 1, wherein the elastic branches and the distal segment lie in a common flat plane.

8. The apparatus according to claim 1, wherein the elastic branches and the distal segment lie in a plurality of planes.

9. The apparatus according to claim 1, wherein the elastic branches are orthogonal to the distal segment.

10. The apparatus according to claim 1, wherein the elastic branches extend non-orthogonally from the distal segment.

11. The apparatus according to claim 1, wherein the distal segment in a relaxed state forms a straight line.

12. The apparatus according to claim 1, wherein the distal segment in a relaxed state forms a curve.

13. The apparatus according to claim 1, wherein in one or more of the plurality of elastic branches the elastic region is more flexible and elastic than the remainder of the elastic branch; and
wherein the remainder of the elastic branch is relatively inelastic and comprises the inelastic region.

14. Apparatus, comprising:
a flexible insertion tube, having a distal segment that is configured to be inserted into a body organ;
a plurality of elastic branches connected to the distal segment of the insertion tube at different, respective locations and extending transversely away from the insertion tube at the respective locations;
one or more respective electrodes disposed on each of the elastic branches; and
conductors traversing the elastic branches so as to couple the electrodes to the insertion tube;
wherein for a cross-sectional circle of the flexible insertion tube only one of the elastic branches is connected to the circle; and
wherein the elastic branches are orthogonal to the distal segment.

15. The apparatus according to claim 14, wherein each of the elastic branches comprises an elastic region and an inelastic region.

16. The apparatus according to claim 14, wherein the elastic branches and the distal segment lie in a common flat plane.

17. The apparatus according to claim 14, wherein the elastic branches and the distal segment lie in a plurality of planes.

18. The apparatus according to claim 14, wherein the distal segment in a relaxed state forms a straight line.

19. The apparatus according to claim 14, wherein the distal segment in a relaxed state forms a curve.

20. Apparatus, comprising:
a flexible insertion tube, having a distal segment that is configured to be inserted into a body organ;
a plurality of elastic branches connected to the distal segment of the insertion tube at different, respective locations and extending transversely away from the insertion tube at the respective locations;
one or more respective electrodes disposed on each of the elastic branches; and
conductors traversing the elastic branches so as to couple the electrodes to the insertion tube;
wherein the elastic branches and the distal segment lie in a common flat plane and elastic branches are orthogonal to the distal segment.

21. The apparatus according to claim 20, wherein each of the elastic branches comprises an elastic region and an inelastic region.

22. The apparatus according to claim 20, wherein the different respective locations of a pair of the elastic branches lie on a cross-sectional circle of the flexible insertion tube.

23. The apparatus according to claim 20, wherein for a cross-sectional circle of the flexible insertion tube only one of the elastic branches is connected to the circle.

24. The apparatus according to claim 20 wherein the body organ comprises a heart, and wherein the one or more respective electrodes are configured to acquire an electrocardiograph (ECG) signal from the heart.

25. The apparatus according to claim 20, wherein the body organ comprises a heart, and wherein the one or more respective electrodes are configured to ablate tissue of the heart.

26. The apparatus according to claim 20, wherein the distal segment in a relaxed state forms a straight line.

27. The apparatus according to claim 20, wherein the distal segment in a relaxed state forms a curve.

28. Apparatus, comprising:
a flexible insertion tube, having a distal segment that is configured to be inserted into a body organ;
a plurality of elastic branches connected to the distal segment of the insertion tube at different, respective locations and extending transversely away from the insertion tube at the respective locations;
one or more respective electrodes disposed on each of the elastic branches; and
conductors traversing the elastic branches so as to couple the electrodes to the insertion tube;
wherein the distal segment in a relaxed state forms a curve.

29. The apparatus according to claim 28, wherein each of the elastic branches comprises an elastic region and an inelastic region.

30. The apparatus according to claim 28, wherein the different respective locations of a pair of the elastic branches lie on a cross-sectional circle of the flexible insertion tube.

31. The apparatus according to claim 28, wherein for a cross-sectional circle of the flexible insertion tube only one of the elastic branches is connected to the circle.

32. The apparatus according to claim 28, wherein the elastic branches and the distal segment lie in a common flat plane.

33. The apparatus according to claim 28, wherein the elastic branches and the distal segment lie in a plurality of planes.

34. The apparatus according to claim 28, wherein the elastic branches are orthogonal to the distal segment.

35. The apparatus according to claim 28, wherein the elastic branches extend non-orthogonally from the distal segment.

36. A method, comprising:
providing a flexible insertion tube, having a distal segment that is configured to be inserted into a body organ;
connecting a plurality of elastic branches to the distal segment of the insertion tube at different, respective locations so that the branches extend transversely away from the insertion tube at the respective locations;
disposing one or more respective electrodes on each of the elastic branches; and
arranging conductors to traverse the elastic branches so as to couple the electrodes to the insertion tube;
wherein each of the elastic branches comprises an elastic region and an inelastic region.

37. The method according to claim 36, wherein on application of a bending force to the each branch, the inelastic region aligns to be parallel to the insertion tube.

38. The method according to claim 36, wherein the different respective locations of a pair of the elastic branches lie on a cross-sectional circle of the flexible insertion tube.

39. The method according to claim 36, wherein for a cross-sectional circle of the flexible insertion tube only one of the elastic branches is connected to the circle.

40. The method according to claim 36, wherein the elastic branches and the distal segment lie in a common flat plane.

41. The method according to claim 36, wherein the elastic branches and the distal segment lie in a plurality of planes.

42. The method according to claim 36, wherein the elastic branches are orthogonal to the distal segment.

43. The method according to claim 36, wherein the elastic branches extend non-orthogonally from the distal segment.

44. The method according to claim 36, wherein the distal segment in a relaxed state forms a straight line.

45. The method according to claim 36, wherein the distal segment in a relaxed state forms a curve.

46. The method according to claim 36, wherein in one or more of the plurality of elastic branches the elastic region is more flexible and elastic than the remainder of the elastic branch; and
wherein the remainder of the elastic branch is relatively inelastic and comprises the inelastic region.

47. A method, comprising:
providing a flexible insertion tube, having a distal segment that is configured to be inserted into a body organ;
connecting a plurality of elastic branches to the distal segment of the insertion tube at different, respective locations so that the branches extend transversely away from the insertion tube at the respective locations;
disposing one or more respective electrodes on each of the elastic branches; and
arranging conductors to traverse the elastic branches so as to couple the electrodes to the insertion tube;
wherein for a cross-sectional circle of the flexible insertion tube only one of the elastic branches is connected to the circle; and
wherein the elastic branches are orthogonal to the distal segment.

48. The method according to claim 47, wherein each of the elastic branches comprises an elastic region and an inelastic region.

49. The method according to claim 47, wherein the elastic branches and the distal segment lie in a common flat plane.

50. The method according to claim 47, wherein the elastic branches and the distal segment lie in a plurality of planes.

51. The method according to claim 47, wherein the distal segment in a relaxed state forms a straight line.

52. The method according to claim 47, wherein the distal segment in a relaxed state forms a curve.

53. A method, comprising:
providing a flexible insertion tube, having a distal segment that is configured to be inserted into a body organ;
connecting a plurality of elastic branches to the distal segment of the insertion tube at different, respective locations so that the branches extend transversely away from the insertion tube at the respective locations;
disposing one or more respective electrodes on each of the elastic branches; and
arranging conductors to traverse the elastic branches so as to couple the electrodes to the insertion tube;
wherein the elastic branches and the distal segment lie in a common flat plane and the elastic branches are orthogonal to the distal segment.

54. The method according to claim 53, wherein each of the elastic branches comprises an elastic region and an inelastic region.

55. The method according to claim 53, wherein the different respective locations of a pair of the elastic branches lie on a cross-sectional circle of the flexible insertion tube.

56. The method according to claim 53, wherein for a cross-sectional circle of the flexible insertion tube only one of the elastic branches is connected to the circle.

57. The method according to claim 53, wherein the distal segment in a relaxed state forms a straight line.

58. The method according to claim 53, wherein the distal segment in a relaxed state forms a curve.

59. A method, comprising:
providing a flexible insertion tube, having a distal segment that is configured to be inserted into a body organ;
connecting a plurality of elastic branches to the distal segment of the insertion tube at different, respective locations so that the branches extend transversely away from the insertion tube at the respective locations;
disposing one or more respective electrodes on each of the elastic branches; and
arranging conductors to traverse the elastic branches so as to couple the electrodes to the insertion tube;
wherein the distal segment in a relaxed state forms a curve.

60. The method according to claim 59, wherein each of the elastic branches comprises an elastic region and an inelastic region.

61. The method according to claim 59, wherein the different respective locations of a pair of the elastic branches lie on a cross-sectional circle of the flexible insertion tube.

62. The method according to claim 59, wherein for a cross-sectional circle of the flexible insertion tube only one of the elastic branches is connected to the circle.

63. The method according to claim 59, wherein the elastic branches and the distal segment lie in a common flat plane.

64. The method according to claim 59, wherein the elastic branches and the distal segment lie in a plurality of planes.

65. The method according to claim 59, wherein the elastic branches are orthogonal to the distal segment.

66. The method according to claim 59, wherein the elastic branches extend non-orthogonally from the distal segment.

* * * * *